United States Patent [19]

Gibbons

[11] 4,032,322

[45] June 28, 1977

[54] ISOTHIAZOLYLFORMAMIDINE DERIVATIVES AS HERBICIDES

[75] Inventor: Loren Kenneth Gibbons, Medina, N.Y.

[73] Assignee: FMC Corporation Phila., Pa.

[22] Filed: June 18, 1976

[21] Appl. No.: 697,456

[52] U.S. Cl. .............................. 71/90; 260/306.8 A
[51] Int. Cl.² ........................................ C07D 275/02
[58] Field of Search ................ 260/306.8 A; 71/90

[56] References Cited
UNITED STATES PATENTS 3,186,999   6/1965   Slack et al. ................. 260/306.8 A

*Primary Examiner*—R. J. Gallagher
*Attorney, Agent, or Firm*—Harrison H. Young, Jr.; Henry R. Ertelt

[57] ABSTRACT

A new class of herbicidal compounds consisting of N'-(substituted-5-isothiazolyl)-N,N-dimethylformamidines in which the 3-substituent on the isothiazole moiety consists of alkyl, alkoxy, alkylthio, alkylsulfinyl, alkylsulfonyl, alkylamino and dialkylamino, and the 4-substituent on the isothiazole moiety consists of cyano, carbamoyl, and nitro, and in which the hydrogen of the dimethylformamidine moiety may be substituted by fluorine, chlorine, bromine, or carbonitrile, exhibits preemergence and postemergence herbicidal activity, controlling effectively the growth of a wide spectrum of grassy and broad-leaved plant species. The synthesis of members of this class is described in detail, and the utility of representative compounds is exemplified.

15 Claims, No Drawings

ISOTHIAZOLYLFORMAMIDINE DERIVATIVES AS HERBICIDES

This invention describes novel herbicidal compounds, new herbicidal compositions, and new methods for preventing and destroying undesired plant growth by post-emergence and preemergence application of said new and useful herbicidal compositions to the locus where control is desired. Effective control of the growth of a variety of grassy and broad-leaved plant species is obtained. At herbicidally effective levels of application, some compounds of the invention show selectivity favorable to corn and related species. The herbicidal compositions may be applied and utilized by commonly accepted methods.

Herbicidal (5-isothiazolyl)urea compounds having a cyano, carboxamide or alkoxycarbonyl group in the 4-position are described in the patent literature. See, for example, Belgian Pat. No. 817,903 and published French application 2,132,191 for compounds in which the 3-substituent of the isothiazole ring is alkyl. Copending applications Ser. No. 697,449, Ser. No. 697,457, and Ser. No. 697,458, filed of even date herewith, describe (5-isothiazolyl(ureas) where the 3-substituent on the isothiazole ring is substituted amino, alkoxy, substituted thio, sulfinyl or sulfonyl, and Ser. No. 697,455 describes (5-isothiazolyl)ureas where the 4-substituent is nitro, also filed of even date herewith. It has now been found that excellent herbicidal activity is obtained by having present on the 5-position, instead of the urea moiety, a formamidine, haloformamidine, or cyanoformamidine moiety. Thus in one aspect of this invention, novel herbicidal compounds contain an isothiazole ring having the following classes of substituents: on the 3-position, an alkyl, alkoxy, substituted amino, alkylthio, alkylsulfinyl or alkylsulfonyl group; on the 4-position, a cyano, carboxamide, alkoxycarbonyl or nitro group; and on the 5-position, a formamidine or substituted formamidine group.

One group of herbicidal compounds in accordance with this invention has the following structure (on which the numbering of the various positions of the isothiazole ring is also indicated):

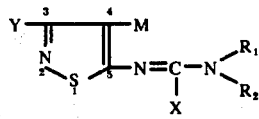

wherein $R_1$ and $R_2$ are lower alkyl or taken together form a divalent radical which may also contain a hetero atom;

M is cyano, carboxamide, alkoxycarbonyl or nitro;

Y is alkyl, alkoxy, alkylthio, alkylsulfinyl, alkylsulfonyl, alkylamino, dialkylamino or a cyclic alkyleneimino group; and X is H, F, Cl, Br or CN.

The alkyl, cycloalkyl and alkenyl groups preferably have less than 10 carbon atoms. Examples of alkyl groups are methyl, ethyl, propyl, isopropyl, isobutyl, sec-butyl, tert-butyl, 2-pentyl, and so forth. The alkylene groups preferably contain a total of four or five catenated atoms, no more than one of which is oxygen, sulfur or nitrogen. In the most preferred compounds, $R_1$ and $R_2$ are methyl, M is cyano, Y is ethyl, isopropyl or tert-butyl, and X is chlorine, bromine, or hydrogen.

The compounds of this invention may be prepared, for example, by the following reaction sequence:

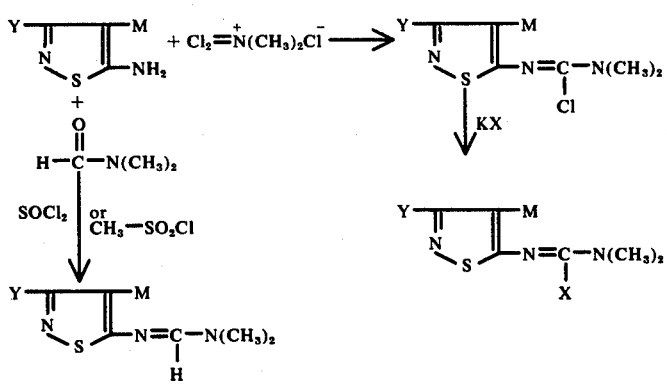

where X is F, Br, or CN.

In th descriptions which follow, all temperatures are in degrees centigrade. All reduced pressures not otherwise designated are pressures normally attainable using a water aspirator.

SYNTHESIS OF INTERMEDIATES

2-Cyano-3-hydroxy-4-methyl-2-pentenenitrile

To a mixture of 132.1 g of malononitrile and 345.6 g of potassium carbonate in 2 liters of methylene chloride was slowly added during 2 hours 316.4 g of isobutyric anhydride. During the addition, the mixture reached the reflux temperature where it was maintained an additional 6.5 hours. The mixture was then stirred at ambient temperature for an additional 15 hours, then chilled to −10°. One liter of concentrated hydrochloric acid was carefully added to the cold mixture, maintaining the temperature below 10° throughout the addition. The acidic mixture was filtered and the layers separated. The water layer was extracted with two 300 ml portions of methylene chloride; the extracts were combined, washed with saturated sodium chloride solution, dried, filtered and concentrated. The solid was collected, washed with pentane and dried to give 195.5 g of 2-cyano-3-hydroxy-4-methyl-2-pentenenitrile, mp 94°–96°. An additional 37 g (mp 87°–90°) was obtained by concentration of the filtrate and washings.

In a similar manner were prepared 2-cyano-3-hydroxy-2-hexenenitrile, liquid purified by distillation on molecular still at 100°/9 mm; 2-cyano-3-hydroxy-4,4-dimethyl-2-pentenenitrile, mp 159°–162°; 2-cyano-3-hydroxy-4,4-dimethyl-2-heptenenitrile, mp 92°–93° (ether-toluene reaction solvent); 2-cyano-3-hydroxy-5-methyl-2-hexenenitrile, liquid purified by molecular distillation at 120°/9 mm; and 2-cyano-3-hydroxy-2-pentenenitrile, liquid purified by molecular distillation at 110°/10–15 mm.

3-Chloro-2-cyano-4,4-dimethyl-2-pentenenitrile

To a solution of 69.6 g of 2-cyano-3-hydroxy-4,4-dimethyl-2-pentenenitrile in 600 ml of methylene chloride was added in small portions 104.1 g of phosphorus pentachloride. The mixture was stirred for 22 hours at room temperature. Sulfur dioxide was passed through the mixture for 20 minutes and the mixture stirred for an additional hour. The mixture was concentrated and poured into 500 ml of ice. After stirring for 1 hour, the cold mixture was filtered, the solid was washed with cold water and dried in a vacuum oven at room temperature for 60 hours to give 68.8 g of 3-chloro-2-cyano-4,4-dimethyl-2-pentenenitrile, mp 52°–53°.

In the same manner were prepared 3-chloro-2-cyano-2-hexenenitrile, bp 73°/1.2 mm; 3-chloro-2-cyano-4-methyl-2-pentenenitrile, bp 52°–58°/0.3 mm; 3-chloro-2-cyano-5-methyl-2-hexenenitrile (used without isolation); 3-chloro-2-cyano-4,4-dimethyl-2-heptenenitrile, an orange-brown liquid used as an intermediate without characterization; and 3-chloro-2-cyano-2-pentenenitrile, bp 57–62°/0.9–2.0 mm.

3-Amino-2-cyano-4-methyl-2-pentenenitrile

A solution of 191.3 g of 3-chloro-2-cyano-4-methyl-2-pentenenitrile in 300 ml of ethanol was added slowly, maintaining the temperature below 40°, during 1.3 hours, to a mixture of 800 ml of concentrated ammonium hydroxide and 1000 ml of ethanol. The mixture was stirred for 3 hours, then poured oer 2000 ml of ice. The solid was collected, washed with water and dried to obtain 122.0 g of 3-amino-2-cyano-4-methyl-2-pentenenitrile, mp 186°–188°.

In the same manner were prepared 3-amino-2-cyano-2-hexenenitrile, mp 133°–135°; 3-amino-2-cyano-4,4-dimethyl-2-pentenenitrile, mp 163°–164°; 3-amino-2-cyano-5-methyl-2-hexenenitrile, mp 113°–116°; 3-amino-2-cyano-4,4-dimethyl-2-heptenenitrile, mp 145°–146°; and 3-amino-2-cyano-2-pentenenitrile, mp 165°–167°.

3Amino-2-cyano-3-propoxypropenenitrile

To a stirred mixture of 129.2 g of potassium tricyanomethanide, 600 g of propanol and 750 ml of dimethoxyethane was added dropwise 96.1 g of methanesulfonic acid during 45 minutes. The exothermic reaction caused the reaction mixture temperature to rise slightly. The volatile materials were removed under reduced pressure and 800 ml of hot water was added to the residue. The solution was treated with charcoal and filtered. The filtrate was evaporated to dryness under reduced pressure. When th residue was allowed to stand at ambient temperature, the product crystallized. The mothr liquor from above was diluted with two volumes of ice, to give additional product. The total yield of 3-amino-2-cyano-3-propoxypropenenitrile was 139 g.

3-Amino-2-cyano-4-methyl-2-pentenethioamide

While maintaining the temperature below 45°, hydrogen sulfide gas was passed for 2 hours into a stirred solution of 122.0 g of 3-amino-2-cyano-4-methyl-2-pentenenitrile and 91.5 g of triethylamino in 122 ml of pyridine. The mixture was stirred for 1 hour at room temperature, then was poured over 2 liters of ice. Th solid was collected, washed with water, dried and recrystallized from ethanol-water to give 128.3 g 3-amino-2-cyano-4-methyl-2-penetenethioamide, mp 112°–114°.

In the same manner were prepared 3-amino-2-cyano-4,4-dimethyl-2-pentenethioamide, mp 129°–131°; 3-amino-2-cyano-2-hexenethioamide, mp 133°–135°; 3-amino-2-cyano-5-methyl-2-hexenethioamide (used as an intermediate without characterization); 3-amino-2-cyano-4,4-dimethyl-2-heptenethioamide, mp 132°–134°; and 3-amino-2-cyano-2-pentenethioamide, mp 104°–107°.

3Amino-2-cyano-3-propoxypropenethioamide

A stirred mixture of 141 g of 3-amino-2-cyano-3-propoxypropenenitrile and 94.4 g of triethylamine in 250 ml of pyridine was heated at 80° for 4 hours while hydrogen sulfide gas was continually passed through the mixture. Thin-layer chromatography indicated reaction to be complete. The reaction mixture was diluted to 2 liters with water and the pale yellow precipitate was collected by filtration. The precipitate was recrystallized from ethanol to give 114 g of 3-amino-2-cyano-3-propoxypropenethioamide, mp 174°.

5-Amino-4-cyano-3-isopropylisothiazole

While maintaining the temperature below 50°, 86.1 g of 30% hydrogen peroxide was added dropwise to a solution of 128.3 g of 3-amino-2-cyano-4-methyl-2-pentenethioamide in 600 ml of absolute ethanol. The mixture was stirred at room temperature for 19 hours, filtered and concentrated to about half volume. Water was added to cloud point and the solid allowed to separate. The solid was collected and dried to give 123.0 g of 5-amino-4-cyano-3-isopropylisothiazole, mp 133°–135°.

In a similar manner were prepared 5-amino-4-cyano-3-propylisothiazole, mp 85°–88°, 5amino-3-tert-butyl-4-cyanoisothiazole, mp 133°–134°, 5-amino-4-cyano-3-isobutylisothiazole, mp 151°–152°, 5-amino-4-cyano-3-(1,1-dimethylbutyl)isothiazole, mp 128°–129°, 5-amino-4-cyano-3-propoxyisothiazole, mp 122°–125°; and 5-amino-4-cyano-3-ethylisothiazole, mp 148°–150°.

EXAMPLE I

N'-(4-Cyano-3-isobutyl-5-isothiazolyl)-N,N-dimethylchloroformamidine

A mixture of 5.4 g of 5-amino-4-cyano-5-isobutylisothiazole and 4.9 g N-(dichloromethylene)-N,N-dimethylammonium chloride in 50 ml of chlorobenzene was placed in a flask equipped with a stirrer. A slow stream of nitrogen was passed through the mixture and into an absorber equipped to measure hydrogen chloride evolution. The mixture was heated at 80° for 1 hour during which time the theoretical amount of hydrogen chloride was evolved. The mixture was allowed to stand under nitrogen atmosphere at ambient temperature for 64 hours, then heated under nitrogen at 80° for 0.5 hours. Thin-layer chromatographic analysis showed two sports, neither corresponding to starting material.

The mixture was cooled to room temperature and concentrated under reduced pressure. The residue was triturated with pentane whereupon a solid formed. Both the solid and the pentatne solution wre found by thin-layer chromatography to contain both components observed in the product. The pentane was removed under reduced pressure and the residue dissolved in cyclohexane. The cyclohexane solution was subjected to chromatographic separation using a 1.25 × 18 inch column containing 100 g of silica gel. Using an eluting solvent containing progressively higher proportion of ethyl acetate, 56 40-ml fractions of eluate were collected. Cuts 11–10 showed no spot in thin-layer chromatography; cuts 11–13 showed one spot; cuts 14–25 showed two spots; cuts 26–35 showed only one spot. The product from cuts 11–13 was found by mass spectrographic analysis to correspond closely to a dimer of 4-cyano-5-[(dimethylamino)-methyleneamino]-3-isobutylisothiazole. The product, 1.4 g, from cuts 26–35 was found by elemental analysis and ir and nmr spectral analysis to be the desired N'-(4-cyano-3-isobutyl-5-isothiazolyl)-N,N-dimethyl-chloroformamidine, m.p. 79°–80°.

Analysis: Calc'd for $C_{11}H_{15}ClN_4S$: C, 48.79; H, 5.58; Cl, 13.09; N, 20.69; S, 11,84; Found: C, 48.88; H, 5.70; Cl, 13.15; N, 20.99; S, 12.57.

EXAMPLE II

N'-(4-Cyano-3-isopropyl-5-isothiazolyl)-N,N-dimethylformamidine

To a solution of 6.7 g of 5-amino-4-cyano-3-isopropylisothiazole in 30 ml of dimethylformamide was slowly added 10.4 ml of thionyl chloride and the mixture was heated under reflux for 3 hours. The mixture was poured into 300 ml of water and the water-dimethylformamide was removed under reduced pressure. The residue was dissolved in ethanol. The solution was treated with decolorizing charcoal, then was diluted with 300 ml of water. The small amount of solid which separated was removed by filtration and was discarded. As the solution stood undisturbed, tan solid separated which was collected and recrystallized from methylcyclohexane to give 3.0 g of N'-(4-cyano-3-isopropyl-5-isothiazolyl)-N,N-dimethylformamidine, m.p. 95°–97°. A small amount was sublimed at 120° under 0.03 mm without change in melting point. The nmr spectrum was consistent with the assigned structure.

Analysis: Calc'd for $C_{10}H_{14}N_4S$: C, 54.03; H, 6.35; N, 25.20; S, 14.42; Found: C, 54.25; H, 6.56; N, 25.25; S, 14.59.

EXAMPLE III

N'-(4-Cyano-3-propoxy-5-isothiazolyl)-N,N-dimethylformamidine

A mixture of 13.7 g of methanesulfonyl chloride in 25 ml of dimethylformamide was stirred at room temperature for about 16 hours. Into the mixture was stirred 11 g of 5-amino-4-cyano-3-propoxyisothiazole which addition caused an exothermic reaction. The mixture was concentrated under reduced pressure and the residue was recrystallized from ethanol to give 2.7 g of crystalline N'-(4-cyano-3-propoxy-5-isothiazolyl)-N,N-dimethylformamidine, m.p. 117°–118°. The nmr spectrum was consistent with the assigned structure.

Analysis:

Calc'd for $C_{10}H_{14}N_4OS$: C, 50.40; H, 5.92; N, 23.51; Found: C, 50.66; H, 6.09; N, 23.45.

EXAMPLE IV

N'-(4-Cyano-3-(1,1-dimethylbutyl)-5-isothiazolyl)-N,N-dimethylformamidine

A solution of 25 g of 5-amino-4-cyano-3-(1,1-dimethylbutyl)isothiazole and 35.6 g of triethyl orthoformate in 200 ml of dioxane was heated under reflux for 2 hours. To the solution was added 24.5 g of acetic anhydride and the mixture was heated under reflux an additional 20 hours. The mixture wss concentrated under reduced pressure and the residue was distilled in a short path still at 120° under 0.1 mm Hg to give 31.8 g of 4-cyano-3-(1,1-dimethylbutyl)-5-[N-(ethoxymethylene)amino]isothiazole which was dissolved in 125 ml of ethanol, without further purification. The ethanolic solution was placed in a flask equipped with a gas inlet tube and one outlet of which was closed by a small rubber balloon. Dimethylamine gas was passed into the solution until the balloon remained inflated; during the introduction of dimethylamine, the temperature of the mixture increased to 60°. The reaction mixture was concentrated under reduced pressure. The residue was recrystallized from a mixture of diethyl ether (90 parts) and pentane (10 parts) at low temperature to give 26.5 g of N'-[4-cyano-3-(1,1-dimethylbutyl)-5-isothiazolyl]-N,N-dimethylformamidine, m.p. 65°–67°. The nmr spectrum was consistent with the assigned structure.

Analysis: Calc'd for $C_{13}H_{20}N_4S$: C, 59.06; H, 7.63; N, 21.19; S, 12.13; Found: C, 59.06; H, 7,87; N, 21.06; S, 12.40.

EXAMPLE V

N'-(4-Cyano-3-propoxy-5-isothiazolyl)-N,N-dimethylchloroformamidine

A mixture of 11 g of 5-amino-4-cyano-3-propoxyisothiazole and 9.8 g of N-(dichloromethylene)-N,N-dimethylammonium chloride in 80 ml of dischloromethane was heated under reflux for about 18 hours. The mixture was concentrated under reduced pressure and the residue was slurried with aqueous sodium bicarbonate solution. The solid was recrystallized from ethanol, then from methylcyclohexane to give 11.3 g of N'-(4-cyano-3propoxy-5-isothiazolyl)-N,N-dimethylchloroformamidine, m.p. 98°–108°. The nmr spectrum was consistent with the assigned structure.

Analysis: Calc'd for $C_{10}H_{13}ClN_4OS$: C, 44.04; H, 4.80; Cl, 13.00; N, 20.54; S. 11.75; Found: C, 45.16; H, 4.78; Cl, 13.01; N, 21.10; S, 11.88.

EXAMPLE VI

N'-(4-Cyano-3-isopropyl-5-isothiazolyl)-N,N-dimethylchloroformamidine

A stirred mixture of 16.7 g of 5-amino-4-cyano-3-isopropylisothiazole and 16.2 g of N-(dichloromethylene)-N,N-dimethylammonium chloride in 100 ml of dichloromethane was heated under reflux during 20 hours. Thin-layer chromatographic analysis of the reaction mixture indicated that reaction was complete. The dichloromethane solvent was evaporated under reduced pressure. To the residue was added 100 ml of saturated sodium bicarbonate solution and 50 ml of ethanol. This mixture was extracted with three 60 ml portions of dichloromethane. The combined extracts were dried over a mixture of anhydrous sodium sulfate and anhydrous magnesium sulfate. The mixture was filtered and the filtrate was evaported under reduced pressure. The residue was washed with 90 ml of diethyl ether followed by a wash with 10 ml of pentane. The precipitate, mp 70°–72°, was collected by filtration. Diethyl ether:pentane (1:1) was added to the filtrate. The filtrate was dried with magnesium sulfate. The mixture was filtered, and the filtrate cooled in an external dry-ice acetone bath, to yield a second crop of solid mp 65°–67°. The combined solids were recrystallized from hexane to yield 13.3 g of N'-(4-cyano-3-isopropyl-5-isothiazolyl)-N,N-dimethylchloroformamidine, mp 72°–75°. The nmr and ir spectra were consistent with the assigned structure.

Analysis: Calc'd for $C_{10}H_{13}N_4ClS$: C, 46.78; H, 5.10; N, 21.82; Found: C, 46.73; H, 5.25; N, 21.86.

In this manner, subsequent runs produced 38.2 g, 133.7 g and 176 g respectively of the chloroformamidine.

EXAMPLE VII

N'-(4-Cyano-3-isopropyl-5-isothiazolyl)-N,N-dimethylfluoroformamidine

A mixture of 12.8 g of N'-(4-cyano-3-isopropyl-5-isothiazolyl)-N,N-dimethylchloroformamidine, 2.9 g of potassium fluoride and a catalytic amount of 2,3,11,12-dibenzo-1,4,7,10,13,16-hexaoxacyclooctadeca-2,11-diene, in 60 ml of acetonitrile was stirred at ambient temperature for 12 hours. The reaction mixture was filtered and the filtrate was evaporated under reduced pressure. The residue was recrystallized from diethyl ether to give 2.5 grams of N'-(4-cyano-3-isopropyl-5-isothiazolyl)-N,N-dimethylfluoroformamidine, mp 100°–102°. The nmr and ir spectra were consistent with the assigned structure.

Analysis: Calc'd for $C_{10}H_{13}N_4FS$: C, 49.98; H, 5.45; N, 23.32; Found: C, 50.15; H, 5.51; N, 23.29.

EXAMPLE VIII

N'-(4Cyano-3-isopropyl-5-isothiazolyl)-N,N-dimethylcyanoformamidine

In the manner of Example VII, 7 g of N'-(4-cyano-3-isopropyl-5-isothiazolyl)-N,N-dimethylchloroformamidine, 3.6 g of anhydrous potassium cyanide, and a catalytic amount of 2,3,11,12-dibenzo-1,4,7,10,13,16-hexaoxacyclooctа-2,11-diene in 200 ml of dry aceto-nitrile were allowed to react for several days. After solvents were removed under reduced pressure, the residue was recrystallized from methylcyclohexane to yield 4.3 g of N'-(4-cyano-3-isopropyl-5-isothiazolyl)-N,N-dimethylcyanoformamidine, mp 78°–79°. The ir and nmr spectra were consistent with the assigned structure.

Analysis: Calc'd for $C_{11}H_{13}N_5S$: C, 53.42; H, 5.30; N, 28.32; S, 12.96; Found: C, 52.99; H, 5.39; N, 27.92; S, 12.58.

EXAMPLE IX

N'-(4-Cyano-3-propyl-5-isothiazolyl)-N,N-dimethylchloroformamidine

In the manner of Example VI, a solution of 8.4 g of 5-amino-4-cyano-3-propylisothiazole in 50 ml of dichloromethane was treated with 9.8 g of N-(dichloromethylene)-N,N-dimethylammonium chloride. After removal of the volatile materials under reduced pressure, the residue was recrystallized from 90:10 hexane:benzene to yield 6.5 g of N'-(4-cyano-3-propyl-5-isothiazolyl)-N,N-dimethylchloroformamidine, mp 108°–109°. The ir and nmr spectra were consistent with the assigned structure.

Analysis Calc'd for: $C_{10}H_{13}ClN_4S$: C, 46.78; H, 5.10; Cl, 13.81; N, 21.82; S, 12.49; Found: C, 46.92; H, 5.26; Cl, 13.59; N, 21.59; S, 12.22.

EXAMPLE X

N'-(3-tert-Butyl-4-cyano-5-isothiazolyl)-N,N-dimethylchloroformamidine

In the manner of Example VI, 9.1 g of 5-amino-3-tert-butyl-4-cyanoisothiazole and 9.8 g of N-(dichloromethylene)-N,N-dimethylammonium chloride were allowed to react in 50 ml of dichloromethane. The volatile materials were evaporated under reduced pressure. The residue was recrystallized from hexane to give 9.2 g of N'-(3-tert-butyl-4-cyano-5-isothiazolyl)-N,N-dimethylchloroformamidine, mp 94°–100°. The ir and nmr spectra were consistent with the assigned structures.

Analysis Calc'd for: $C_{11}H_{15}ClN_4S$: C, 48.79; H, 5.58; Cl, 13.09; N, 20.69; S, 11.84; Found: C, 49.05; H, 5.66; Cl, 12.90; N, 20.92; S, 11.78.

EXAMPLE XI

N'-(4-Cyano-3-isopropyl-5-isothiazolyl)-N,N-dimethylbromoformamidine

To a solution of 22.8 g of N'-(4-cyano-3-isopropyl-5-isothiazolyl)-N,N-dimethylurea in 300 ml of benzene was added 83.3 g of phosphorous oxybromide. The solution was cooled to 0° and 14 ml (9.7 g) of triethylamine was added. The ice-bath was removed and the reaction mixture was heated under reflux overnight. The following day the reaction mixture was filtered through sintered glass. The filtrate was washed with two 200 ml portions of cold water and two 200 ml portions of saturated sodium bicarbonate solution. Two hundred milliliters of chloroform was added to aid in separation of the organic phase from the final wash. The separated organic phase was dried, then concentrated under reduced pressure. The residue was passed over a column of 300 grams of silica gel with chloroform as the eluant. The first 10 250 ml fractions were evaporated to produce a yellow solid, mp 93°–97°. The combined residues were recrystallized from 175 ml of cyclohexane to yield 13.8 g of N'-(4-cyano-3-isopropyl-5-isothiazolyl)-N,N-dimethylbromoformamidine mp 92°–96°. The ir and nmr spectra were consistent with the assigned structure.

Analysis Calc'd for:
$C_{10}H_{13}BrN_4S$: C, 39.87; H, 4.35; Br, 26.53; N, 18.60; S, 10.64;

Found: C, 39.62; H, 4.40; Br, 26.37; N, 18.53; S, 10.68.

EXAMPLE XII

N'-(4-Cyano-3-ethyl-5-isothiazolyl)-N,N-dimethylchloroformamidine

In the manner of Example VI, 7.6 g of 5-amino-4-cyano-3-ethylisothiazole and 8.1 g of N-(dichloromethylene)-N,N-dimethylammonium chloride were allowed to react in 100 ml of dichloromethane. The volatile materials were evaporated under reduced pressure. The residue was recrystallized twice from cyclohexane to give 2.0 g of N'-(4-cyano-3-ethyl-5-isothiazolyl)-N,N-dimethylchloroformamidine, mp 95°–97°. The nmr spectrum was consistent with the assigned structure.

Analysis Calc'd for:
$C_9H_{11}N_4ClS$: C, 44.53; H, 4.57; Cl, 14.61; N, 23.08; S, 13.21;

Found: C, 44.59; H, 4.48; Cl, 14.69; N, 23.06; S, 13.03.

The herbicidal activities of the compounds of this invention were demonstrated as follows. In preemergence tests, rows of seeds of lima beans (*Phaseolus lunatus*), corn (*Zea mays*), wild oats (*Avena fatua*), lettuce (*Lactuca sativa*), mustard (*Brassica juncea*) and crabgrass (*Digitaria sanguinalis*) were planted in shallow flat-bed trys (20 cm × 15 cm × 7.5 cm) containing 5 cm to 7.5 cm of sandy loam soil. Within 24 hours after planting, an aqueous acetone solution of the compound (using sufficient acetone to obtain solution) was sprayed on the soil at a rate equivalent to 8.96 kilograms per hectare, 4.48 kg, 2.24 kg, 0.56 kg, and 0.28 kg/hectare, using a total volume equivalent to 760 liters per hectare. The trays were maintained under normal growing conditions in the greenhouse for about 3 weeks, after which the herbicidal efficacy of the compound was assessed. Individual plant species were examined in comparison with untreated plants. Table 1 lists data collected in preemergence tests with compounds of the present invention.

In postemergence tests, rows of seeds were planted as for preemergence tests and the untreated flats were maintained in the greenhouse until the first trifoliate leaves of the bean plants were unfolding. The test plants were then sprayed with an aqueous acetone solution of the compound as for preemergence tests. The plants were returned to the greenhouse and held under normal growing conditions for about 3 more weeks, after which the herbicidal efficacy of the compound was assessed. Table 2 lists data collected in postemergence tests with compounds of the present invention.

An evaluation of the preemergence herbicidal activity of the compound of Example VI was carried out employing a broader range of plants. The techniques utilized were as described for the preemergence tests above. Results are collected in Table 3.

Table 1

Preemergence Herbicidal Activity of Isothiazolylformamidines
(expressed as % kill at indicated rate in kg/hectare)

| Compound of Example | Rate | Lima Beans | Corn | Wild Oats | Lettuce | Mustard | Crabgrass |
|---|---|---|---|---|---|---|---|
| I | 2.24 | 100 | 0 | 50 | 100 | 100 | 100 |
|   | 1.12 | 100 | 0 | 30 | 100 | 100 | 80 |
|   | 0.56 | 0 | 0 | 0 | 70 | 80 | 30 |
|   | 0.28 | 0 | 0 | 0 | 50 | 70 | 0 |
| II | 8.96 | 100 | 0 | 10 | 100 | 100 | 30 |
|   | 4.48 | 100 | 0 | 70 | 100 | 100 | 0 |
|   | 2.24 | 100 | 0 | 30 | 100 | 80 | 0 |
|   | 1.12 | 100 | 0 | 60 | 100 | 100 | 0 |
|   | 0.56 | 100 | 0 | 40 | 100 | 50 | 50 |
|   | 0.28 | 100 | 0 | 30 | 100 | 20 | 0 |
| III | 8.96 | 0 | 0 | 0 | 30 | 0 | 0 |
|   | 4.48 | 0 | 0 | 0 | 0 | 0 | 0 |
|   | 2.24 | 0 | 0 | 0 | 0 | 0 | 0 |
|   | 1.12 | 0 | 0 | 0 | 0 | 0 | 0 |
|   | 0.56 | 0 | 0 | 0 | 0 | 0 | 0 |
|   | 0.28 | 0 | 0 | 0 | 0 | 0 | 0 |
| IV | 8.96 | 0 | 0 | 50 | 0 | 50 | 0 |
|   | 4.48 | 0 | 0 | 0 | 0 | 0 | 0 |
|   | 2.24 | 0 | 0 | 0 | 0 | 0 | 0 |
|   | 1.12 | 0 | 0 | 0 | 0 | 0 | 0 |
|   | 0.56 | 0 | 0 | 0 | 0 | 0 | 0 |
|   | 0.28 | 0 | 0 | 0 | 0 | 0 | 0 |
| V | 8.96 | 100 | 0 | 0 | 100 | 100 | 0 |
|   | 4.48 | 75 | 0 | 0 | 30 | 0 | 0 |
|   | 2.24 | 0 | 0 | 0 | 0 | 0 | 0 |
|   | 1.12 | 0 | 0 | 0 | 0 | 0 | 0 |
|   | 0.56 | 0 | 0 | 0 | 0 | 0 | 0 |
|   | 0.28 | 0 | 0 | 0 | 0 | 0 | 0 |
| VI | 8.96 | 100 | 100 | 100 | 100 | 100 | 100 |
|   | 4.48 | 100 | 100 | 80* | 100 | 100 | 100 |
|   | 2.24 | 100 | 0 | 80 | 100 | 100 | 30 |
|   | 1.12 | 100 | 0 | 70 | 100 | 100 | 10 |
|   | 0.56 | 100 | 0 | 50 | 90* | 100 | 0 |
|   | 0.28 | 100 | 0 | 30 | 90* | 100 | 0 |
| VII | 8.96 | 100 | 30 | 90* | 100 | 100 | 90* |
|   | 4.48 | 100 | 0 | 25 | 100 | 100 | 90* |
|   | 2.24 | 100 | 0 | 50 | 100 | 100 | 80 |
|   | 1.12 | 100 | 0 | 0 | 75 | 90* | 20 |
|   | 0.56 | 0 | 0 | 0 | 0 | 0 | 0 |
|   | 0.28 | — | — | — | — | — | — |
| VIII | 8.96 | 100 | 0 | 100 | 100 | 100 | 95* |
|   | 4.48 | 100 | 0 | 100 | 100 | 100 | 20 |
|   | 2.24 | 90* | 0 | 30 | 100 | 100 | 20 |
|   | 1.12 | 90* | 0 | 20 | 100 | 100 | 0 |
|   | 0.56 | 20 | 0 | 0 | 90* | 80 | 0 |
|   | 0.28 | 0 | 0 | 0 | 40 | 75 | 0 |
| IX | 8.96 | 100 | 100 | 100 | 100 | 100 | 95* |
|   | 4.48 | 100 | 90* | 100 | 100 | 100 | 95* |
|   | 2.24 | 100 | 0 | 100 | 100 | 100 | 95* |
|   | 1.12 | 95* | 0 | 95* | 100 | 100 | 95* |
|   | 0.56 | 100 | 0 | 95* | 100 | 95* | 0 |
|   | 0.28 | 40 | 0 | 0 | 90* | 0 | 0 |
| X | 8.96 | 100 | 100 | 100 | 100 | 100 | 95* |
|   | 4.48 | 100 | 95* | 100 | 100 | 100 | 95* |
|   | 2.24 | 100 | 30* | 100 | 100 | 100 | 95* |
|   | 1.12 | 100 | 0 | 100 | 100 | 100 | 50 |
|   | 0.56 | 100 | 0 | 30 | 100 | 100 | 0 |
|   | 0.28 | 100 | 0 | 0 | 40 | 95* | 0 |
| XI | 8.96 | 100 | 70 | 100 | 100 | 100 | 100 |
|   | 4.48 | 100 | 0 | 100 | 100 | 100 | 100 |
|   | 2.24 | 100 | 0 | 100 | 100 | 100 | 100 |
|   | 1.12 | 100 | 0 | 70 | 100 | 100 | 100 |
|   | 0.56 | 100 | 0 | 20 | 100 | 50 | 100 |
|   | 0.28 | 75 | 0 | 0 | 100 | 100 | 50 |
| XII | 8.96 | 100 | 70* | 100 | 100 | 100 | 100 |
|   | 4.48 | 100 | 30* | 100 | 100 | 100 | 100 |
|   | 2.24 | 100 | 0 | 100 | 100 | 100 | 100 |
|   | 1.12 | 100 | 0 | 100 | 100 | 100 | 80 |
|   | 0.56 | 100 | 0 | 70 | 100 | 100 | 50 |
|   | 0.28 | 100 | 0 | 50 | 100 | 100 | 100 |

*Plants not dead were severely damaged and not expected to live.

Table 2

Postemergence Herbicidal Activity of Isothiazolylformamidines
(expressed as % kill at 8.96 kg/hectare)

| Compound of Example | Lima Beans | Corn | Wild Oats | Lettuce | Mustard | Crabgrass |
|---|---|---|---|---|---|---|
| I | 100 | 30 | 100 | 100 | 100 | 100 |
| II | 100 | 0 | 10 | 100 | 100 | 10 |
| III | 0 | 0 | 0 | 0 | 0 | 0 |
| IV | 0 | 0 | 0 | 100 | 100 | 0 |
| V | 50 | 0 | 0 | 100 | 50 | 0 |
| VI | 100 | 100 | 100 | 100 | 100 | 100 |
| VII | 100 | 75 | 100 | 100 | 100 | 90* |
| VIII | 100 | 0 | 100 | 100 | 100 | 90* |
| IX | 100 | 60* | 100 | 100 | 100 | 95* |
| X | 100 | 0* | 100 | 100 | 100 | 95* |
| XI | 100 | 100 | 100 | 100 | 100 | 100 |
| XII | 100 | 100 | 100 | 100 | 100 | 100 |

*Plants not dead were severely damaged and not expected to live.

Table 3

Preemergence Herbicidal Activity of Isothiazolylformamidine of Example VI
(expressed as % kill at indicated rate in kg/hectare)

| | 0.28 | 0.56 | 1.12 | 2.24 | 4.48 |
|---|---|---|---|---|---|
| Corn | 0 | 0 | 0 | 70 | 100 |
| Morning Glory | 90* | 100 | 100 | 100 | 100 |
| Morning Glory | 100 | 50* | 60* | 50* | 50* |
| Giant Foxtail | 0 | 20 | 100 | 100 | 100 |
| Giant Foxtail | 40 | 70 | 100 | 100 | 100 |

Table 3-continued

Preemergence Herbicidal Activity
of Isothiazolylformamidine of Example VI
(expressed as % kill at indicated rate
in kg/hectare)

|  | 0.28 | 0.56 | 1.12 | 2.24 | 4.48 |
|---|---|---|---|---|---|
| Crabgrass | 0 | 30 | 70* | 100 | 100 |
| Crabgrass | 0 | 100 | 100 | 100 | 100 |
| Barnyardgrass | 50 | 80 | 90* | 95* | 90* |
| Barnyardgrass | 30 | 80* | 100 | 100 | 100 |
| Soybean | 100 | 100 | 100 | 100 | 100 |
| Wheat | 30 | 50 | 100 | 100 | 100 |
| Barley | 30 | 50 | 100 | 100 | 100 |
| Prickly Sida | — | 50 | 100 | 100 | 100 |
| Sugar Beet | 70 | 100 | 100 | 100 | 100 |
| Flax | 0 | 0 | 70 | 100 | 100 |
| Peanut | 0 | 0 | 100 | 100 | 100 |
| Sicklepod | 30 | 70 | 100 | 100 | 100 |
| Downy Brome | 50 | 50 | 90* | 100 | 100 |
| Coffeeweed | 100 | 100 | 100 | 100 | 100 |
| Tomato | 0 | 0 | 100 | 100 | 100 |
| Sorghum | 0 | 0 | 30 | 70* | 100 |
| Oats | 70* | 100 | 100 | 100 | 100 |
| Rice | 100 | 100 | 100 | 100 | 100 |
| Cotton | 75 | 100 | 100 | 100 | 100 |
| Purple Nutsedge | 0 | 0 | 0 | 0 | 25 |

*Plants not dead were severely damaged and not expected to live.

For herbicidal application, the compounds of this invention may be utilized in diverse formulations including the agricultural adjuvants and agricultural carriers, i.e. those materials normally employed to facilitate the dispersion of active ingredients in agricultural applications, recognizing the fact that the formulation and mode of application of a toxicant may affect the activity of the material in a given application. Thus, a compound of this invention may be formulated as a granule of relatively large particle size, as a wettable powder, as an emulsifiable concentrate, as a solution, or as any of several other known types of formulations, depending on the desired mode of application.

Granular formulations are particularly useful for aerial distribution or for penetration of a canopy of foiliage. Useful granular formulations may be of several types. Impregnated granules are those wherein the active ingredient is applied to large particles of an absorbent carrier, such as an attapulgite or kaolin clay, corncobs, expanded mica, and so forth, normally in the form of a solution is a solvent. Surface-coated granules may be produced by spraying the molten active ingredient onto the surface of a generally non-absorbent particle or by spraying on a solution of active ingredient in a solvent. The core may be water-soluble such as a prilled fertilizer, or insoluble such as sand, marble chips or coarse talc. Particularly useful is a granule wherein a wettable powder is applied as a surface coating to a sand or other insoluble particle such that the wettable powder may be dispersed on contact of the granule with moisture. Granules may be produced by agglomeration of dusts of powders by compaction rollers, by extrusion through a die or by use of a granulating disc. Granular formulations may vary widely in concentration, with useful formulations containing as little as 0.5% or as much as 95% of active ingredient.

Wettable powders, also useful formulations for both pre- and postemergence herbicides, are in the form of finely divided particles which disperse readily in water or other dispersants. The wettable powder is ultimately applied to the soil or to the undesired plant growth either as a finely divided dry material or as an emulsion in water or other liquid. Typical carriers for wettable powders include fuller's earth, kaolin clays, silicas and other highly absorbent, readily wet inorganic diluents. Wettable powders normally are prepared to contain about 5% to 80% of active ingredient, depending on the abosrbency of the carrier, and usually also contain a small amount of a wetting, dispersing or emulsifying agent of factilitate dispersion. For example, a useful wettable powder formulation contains 80.8 parts of N'-(4-cyano-3-isopropyl-5-isothiazolyl) -N,N-dimethylformamidine, 17.9 parts of palmetto clay, and 1.0 part of sodium lignosulfonate and 0.3 part of sulfonated aliphatic polyester as wetting agents.

Other useful formulations for herbicidal applications are the emulsifiable concentrates, which are homogeneous liquid or paste compositions dispersible in water or other dispersant, and may consist entirely of a compound of this invention with a liquid or solid emulsifying agent, or may also contain an agriculturally acceptable liquid carrier, such as xylene, heavy aromatic naphthas, isophorone and other nonvolatile organic solvents.

Typical wetting, dispersing or emulsifying agents used in agricultural formulations include, for example, the alkyl and alkylaryl sulfonates and sulfates and their sodium salts; polyethylene oxides; sulfonated oils; fatty acid esters of polyhydric alcohols; and other types of surface-active agents, many of which are available in commerce. The surface-active agent, when used, normally comprises from 1% to 15% by weight of the herbicidal composition.

These formulations may be applied without further dilution or as dilute solutions, emulsions or suspensions in water or other suitable diluent. The compositions may be applied to the area wherein control is desired by spraying onto the undesired vegetation or onto the surface of the soil in the case of liquid compositions or by distribution from mechanical equipment in the case of solids. The surface-applied material may also be blended into the upper layer of soil by cultivation, or left as applied, as is appropriate to gain the optimum results with the particular treatment.

The active herbicidal compounds of this invention may be formulated and/or applied with insecticides, fungicides, nematicides, plant regulators, fertilizers, and other agricultural chemicals. In applying the active compounds of this invention, whether formulated along or with other agricultural chemicals, an effective amount and concentration of isothiazolyl compound is of course employed.

It is apparent that various modifications may be made in the formulation and application of the novel compounds of this invention, without departing from the inventive concept herein, as defined in the following claims:

I claim:

1. A substituted formamidine of the formula:

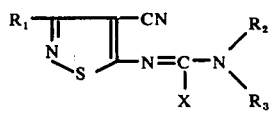

in which $R_1$ is a straight or branched alkyl of 1 to 4 carbons; $R_2$ and $R_3$ are alkyl of 1 to 4 carbons; and X is hydrogen, fluorine, chlorine, bromine, or carbonitrile.

2. The compound of claim 1 in which X is hydrogen.
3. The compound of claim 2 which is N'-(4-cyano-3-isopropyl-5-isothiazolyl)-N,N-dimethylformamidine.
4. The compound of claim 1 in which X is chlorine.

5. The compound of claim 4 which is N'-(4-cyano-3-isopropyl-5-isothiazolyl)-N,N-dimethylchloroformamidine.

6. The compound of claim 4 which is N'-(4-cyano-3-isobutyl-5-isothiazolyl)-N,N-dimethylchloroformamidine.

7. The compound of claim 4 which is N'-(4-cyano-3-propyl-5-isothiazolyl)-N,N-dimethylchloroformamidine.

8. The compound of claim 4 which is N'-(4-cyano-3-tert-butyl-5-isothiazolyl)-N,N-dimethylchloroformamidine.

9. The compound of claim 4 which is N'-(4-cyano-3-ethyl-5-isothiazolyl)-N,N-dimethylchloroformamidine.

10. The compound of claim 1 in which X is carbonitrile.

11. The compound of claim 10 which is N'-(4-cyano-3-isopropyl-5-isothiazolyl)-N,N-dimethylcyanoformamidine.

12. The compound of claim 1 in which X is bromine.

13. The compound of claim 12 which is N'(4-cyano-3-isopropyl-5-isothiazolyl)-N,N-dimethylbromoformamidine.

14. An herbicidal composition comprising an herbicidally effective amount of a compound of claim 1 in admixture with an agriculturally acceptable extender.

15. A method of preventing and destroying plant growth which comprises applying to the locus to be protected an herbicidally effective amount of a compound of claim 1.

* * * * *

UNITED STATES PATENT AND TRADEMARK OFFICE
CERTIFICATE OF CORRECTION

PATENT NO. : 4,032,322
DATED : June 28, 1977
INVENTOR(S) : L. K. Gibbons

It is certified that error appears in the above—identified patent and that said Letters Patent is hereby corrected as shown below:

Column 1, line 41, "(5-isothiazolyl(ureas)" should read --(5-isothiazolyl)ureas--. Column 3, line 15, "hours" should read --horus--; line 41, "poured oer" should read --poured over--. Column 5, line 2, "two sports," should read --two spots, --; line 6, "the pentatne solution wre", should read --the pentane solution were--; line 15, "Cuts 11-10" should read --Cuts 1-10--; line 27, "S, 11,84;" should read --S, 11.84;--. Column 6, line 41, "dischlorome-" should read --dichlorome- --. Column 7, line 3, "evaported" should read --evaporated--; line 41, "N'-(4Cyano-3-isopropyl-5-isothiazolyl)-N,N-dimethyl-" should read --N'-(4-Cyano-3-isopropyl-5-isothiazolyl)-N,N-dimethyl- --. Column 8, line 9, "N'-3-tert-Butyl-4-cyano-5-isothiazolyl)-N,N-dime-" should read --N'-(3-tert-Butyl-4-cyano-5-isothiazolyl)-N,N-dime- --; line 31, "83.3 g" should read --82.3 g--. Column 9, line 14, "flat-bed trys" should read --flat-bed trays--. Column 11, line 38, "foiliage." should read --foliage.--; line 43, "is a solvent." should read --in a solvent.--; line 54, "of dusts of powders" should read --of dusts or powders--. Column 12, line 2, "abosrbency" should read --absorbency--; line 4, "agent of factilitate" should read --agent to facilitate--; line 44, "formulated along" should read --formulated alone--. Column 14, line 7, "N'(4-cyano-" should read --N'-(4-cyano- --.

Signed and Sealed this

Eighteenth Day of November 1980

[SEAL]

Attest:

SIDNEY A. DIAMOND

Attesting Officer  Commissioner of Patents and Trademarks